(12) United States Patent
Wassmund et al.

(10) Patent No.: US 6,584,356 B2
(45) Date of Patent: Jun. 24, 2003

(54) DOWNLOADABLE SOFTWARE SUPPORT IN A PACEMAKER

(75) Inventors: Paul G. Wassmund, Bethel, MN (US); Paul A. Penrose, Hastings, MN (US); Donald Johnson, Lino Lakes, MN (US); Jeffrey David Wilkinson, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 234 days.

(21) Appl. No.: 09/755,425

(22) Filed: Jan. 5, 2001

(65) Prior Publication Data

US 2002/0091416 A1 Jul. 11, 2002

(51) Int. Cl.[7] .................................................. A61N 1/20
(52) U.S. Cl. .......................... 607/30; 607/4; 607/9; 607/55
(58) Field of Search ........................ 607/4, 5, 9, 30, 607/55

(56) References Cited

U.S. PATENT DOCUMENTS

| | | |
|---|---|---|
| 4,211,235 A | 7/1980 | Keller, Jr. et al. |
| 4,357,943 A | 11/1982 | Thompson et al. |
| 4,374,382 A | 2/1983 | Markowitz |
| 4,476,868 A | 10/1984 | Thompson |
| 4,539,992 A | 9/1985 | Calfee et al. |
| 4,550,732 A | 11/1985 | Batty, Jr. et al. |
| 4,556,063 A | 12/1985 | Thompson et al. |
| 4,571,589 A | 2/1986 | Slocum et al. |
| 4,676,248 A | 6/1987 | Berntson |
| 5,052,388 A | 10/1991 | Sivula et al. |
| 5,127,404 A | 7/1992 | Wyborny et al. |
| 5,345,362 A | 9/1994 | Winkler |
| 5,843,138 A | * 12/1998 | Evers et al. ................ 607/30 |
| 5,891,179 A | * 4/1999 | Er et al. ..................... 607/27 |
| 5,893,066 A | * 4/1999 | Hong ......................... 704/500 |
| 5,949,410 A | * 9/1999 | Fung ........................ 707/500.1 |
| 6,083,248 A | * 7/2000 | Thompson ................. 607/30 |
| 6,358,202 B1 | * 3/2002 | Arent ......................... 600/300 |
| 6,386,882 B1 | * 5/2002 | Linberg ...................... 434/262 |
| 2002/0009149 A1 | * 1/2002 | Rodriguez et al. ..... 375/240.25 |

* cited by examiner

*Primary Examiner*—Hieu T. Vo
*Assistant Examiner*—Johnny H. Hoang
(74) *Attorney, Agent, or Firm*—Girma Wolde-Michael

(57) ABSTRACT

A method is provided, the method comprising controlling an implantable medical device using a controller using a pre-emptive real-time operating system (RTOS) having a scheduling mechanism utilizing a priority inheritance protocol, the controller having a firmware architecture allowing at least one of modular feature design, modular feature implementation, extensible feature design and extensible feature implementation. The device also comprises analyzing the pre-emptive real-time operating system (RTOS) using rate monotonic analysis, providing an interface with downloadable software for the implantable medical device and backing up at least some of the downloadable software using a non-volatile memory device, protecting the at least some of the downloadable software from a reset of the implantable medical device.

24 Claims, 12 Drawing Sheets

DOWNLOADABLE SOFTWARE SUPPORT IN A PACEMAKER

BACKGROUND OF THE INVENTION

1. Field of the Invention

This invention relates generally to implantable medical devices and, more particularly, to a firmware architecture permitting modular feature design for implantable medical devices.

2. Description of the Related Art

Since the introduction of the first implantable pacemakers in the 1960s, there have been considerable advances in both the fields of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than earlier ones. Today's state-of-the-art implantable medical devices are capable of performing significantly more complex tasks. The therapeutic benefits of such devices have been well proven.

As the functional sophistication and complexity of implantable medical device systems have increased over the years, it has become increasingly useful to include a system for facilitating communication between one implanted device and another implanted or external device, for example, a programming console, monitoring system, or the like. Shortly after the introduction of the earliest pacemakers, it became apparent that it would be desirable for physicians to non-invasively obtain information regarding the operational status of the implanted device, and/or to exercise at least some control over the device, e.g., to turn the device on or off or adjust the pacing rate, after implant. As new, more advanced features have been incorporated into implantable devices, it has been increasingly useful to convey correspondingly more information to/from the device relating to the selection and control of those features.

In particular, implantable pacemaker therapies have grown in number and complexity. In conventional devices this growth in the number and complexity of the various implantable pacemaker therapies has led to numerous feature interactions. These feature-to-feature interactions may adversely affect the efficacy of various of the implantable pacemaker therapies. Additionally, conventional devices have provided support for downloadable software, also known as random access memory-ware (RAMware), but the RAMware designs for conventional devices typically are uniform, documented in the product specification, firmware functional design and code listings, "set in stone" as it were. Consequently, the RAMware designs for conventional devices typically are difficult to design and/or implement and are relatively inflexible and expensive to reprogram, change and/or improve. For example, a set of "patch points" are provided, a fixed number of points in the code where "patch" code could be checked for and, if present, executed.

These patch points typically are not in locations best suited for a particular RAMware application, resulting in a limitation of the functionality of the RAMware application. This limitation of the functionality of the RAMware application has typically made RAMware impractical for many complex features, restricting the use of RAMware to primarily short-term research tools. This limitation of the functionality of the RAMware application could also inflate the size of a patch, since a large block of code that had been bypassed often needed to be replicated to achieve the desired functionality. Since the RAMware applications have to reside among the existing "tasks" in the embedded firmware, the RAMware applications could also create timing problems, making it difficult for the firmware to achieve all of the firmware deadlines. Additionally, there is typically no way to preserve and/or back up a RAMware application through a device reset.

Furthermore, feature interactions are difficult to manage in conventional implantable pacemakers. Typically, multiple therapy features, such as Mode Switch (MS) and Rate Drop Response (RDR), are not able to operate at the same time. To resolve adverse feature-to-feature interactions, specific features are typically forced "off" (either by the programmer or within the conventional implantable pacemaker) when another feature is turned "on." Additionally, these complex feature interactions, particularly in brady and tachy devices, lead to slow and difficult development of feature addition, modification and/or removal, because the features are neither modular nor extensible and cannot easily be added, modified and/or removed from conventional implantable pacemakers during development.

The present invention is directed to overcoming, or at least reducing the effects of, one or more of the problems set forth above.

SUMMARY OF THE INVENTION

In one aspect of the present invention, a method is provided, the method comprising controlling an implantable medical device using a controller using a pre-emptive real-time operating system (RTOS) having a scheduling mechanism, the controller having a firmware architecture allowing at least one of modular feature design, modular feature implementation, extensible feature design and extensible feature implementation. The method also comprises analyzing the pre-emptive real-time operating system (RTOS) using rate monotonic analysis, providing an interface with downloadable software for the implantable medical device and backing up at least some of the downloadable software using a non-volatile memory device, protecting at least some of the downloadable software from a reset of the implantable medical device.

In another aspect of the present invention, a device is provided, the device comprising an implantable medical device and a controller controlling the implantable medical device, the controller using a pre-emptive real-time operating system (RTOS) having a scheduling mechanism, the controller having a firmware architecture allowing at least one of modular feature design, modular feature implementation, extensible feature design and extensible feature implementation, the pre-emptive real-time operating system (RTOS) capable of being analyzed using rate monotonic analysis. The device also comprises an interface interfacing with downloadable software for the implantable medical device and a non-volatile memory device capable of protecting at least some of the downloadable software from a reset of the implantable medical device.

In yet another aspect of the present invention, a device is provided, the device comprising means for controlling an implantable medical device using a controller using a pre-emptive real-time operating system (RTOS) having a scheduling mechanism, the controller having a firmware architecture allowing at least one of modular feature design, modular feature implementation, extensible feature design and extensible feature implementation. The device also comprises means for analyzing the pre-emptive real-time operating system (RTOS) using rate monotonic analysis, means for providing an interface with downloadable software for the implantable medical device and means for backing up at least some of the downloadable software using a non-volatile memory device, protecting the at least some of the downloadable software from a reset of the implantable medical device.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIG. 1 schematically illustrates an implantable medical device (IMD) system according to the present invention;

FIG. 2 schematically illustrates a general block diagram of electronic circuitry for the implantable medical device (IMD) system of FIG. 1;

FIG. 3 schematically illustrates a perspective view of one embodiment of the programming unit for the implantable medical device (IMD) system of FIG. 1;

FIG. 4 schematically illustrates a general block diagram of various illustrative embodiments of a method and a device according the present invention comprising an implantable medical device (IMD) and an implantable medical device (IMD) controller using a pre-emptive real-time operating system (RTOS), the controller having a firmware architecture allowing at least one of modular feature design, modular feature implementation, extensible feature design and extensible feature implementation;

FIG. 5 schematically illustrates an implantable medical device (MD) controller having a plurality of modular features;

FIG. 6 schematically illustrates controlling an implantable medical device (IMD) using an implantable medical device (IMD) controller by adding a modular feature to lower level firmware;

FIG. 7 schematically illustrates controlling an implantable medical device (IMD) using an implantable medical device (IMD) controller by modifying a modular feature in lower level firmware;

FIG. 8 schematically illustrates controlling an implantable medical device (IMD) using an implantable medical device (IMD) controller by deleting a modular feature from lower level firmware;

FIG. 9 schematically illustrates an implantable medical device (IMD) controller using a pre-emptive real-time operating system (RTOS) having a scheduling mechanism, a downloadable software interface and a non-volatile memory;

FIG. 10 schematically illustrates an implantable medical device (IMD) controller using a pre-emptive real-time operating system (RTOS) having a scheduling mechanism with a priority inheritance protocol, a downloadable software interface and a non-volatile memory;

FIG. 11 schematically illustrates an implantable medical device (IMD) controller using a pre-emptive real-time operating system (RTOS) having a scheduling mechanism, a downloadable software interface with call tables and an electrically erasable programmable read-only memory (EEPROM) non-volatile memory; and FIG. 12 schematically illustrates an implantable medical device (IMD) controller using a pre-emptive real-time operating system (RTOS) having a scheduling mechanism with a priority inheritance protocol, a downloadable software interface with call tables and an electrically erasable programmable read-only memory (EEPROM) non-volatile memory.

Figure 1:
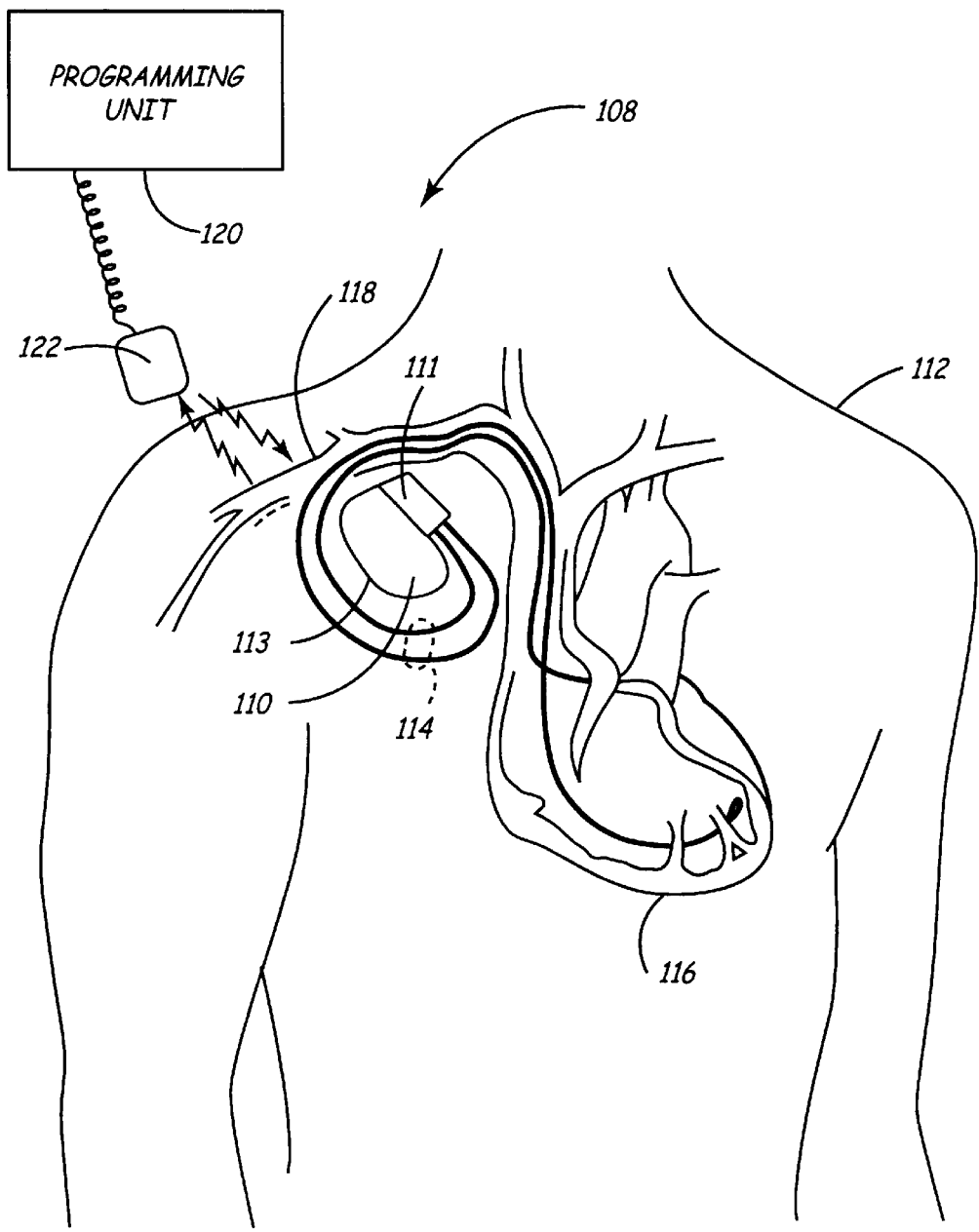
FIGS. 1–12 schematically illustrate various embodiments of a method and a device according to the present invention; and, more particularly.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of an apparatus and a method for operation of the apparatus according to the present invention are shown in FIGS. 1–12. FIG. 1 illustrates an implantable medical device (IMD) system 108, which includes, for example, an implantable pacemaker 110 that has been implanted in a patient 112. The pacemaker 110 is housed within a hermetically sealed, biologically inert outer canister or housing 113, which may itself be conductive so as to serve as an electrode in the pacemaker's pacing/sensing circuit. One or more pacemaker leads, collectively identified with reference numeral 114 in FIG. 1 are electrically coupled to the pacemaker 110 in a conventional manner and extend into the patient's heart 116 via a vein 118. Disposed generally near a distal end of the leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

Although the present invention is described herein in an embodiment that includes a pacemaker, it may be advantageously embodied in numerous other types of implantable medical device systems in which it is desirable to provide a communication link between two physically separated components and retrieve data stored therein.

FIG. 1 also depicts an external programming unit 120 for non-invasive communication with the implanted device 110 via conventional uplink and downlink communication channels, which are not described in greater detail herein so as to avoid unnecessarily obscuring the instant invention. Associated with the programming unit 120 is a programming head 122, in accordance with conventional medical device programming systems, for facilitating two-way communication between the pacemaker 110 and the programmer 120. In many known implantable device systems, the programming head 122, such as that depicted in FIG. 1, is positioned on the patient's body over the implant site of the device 110 (usually within about 2 to about 3 inches, or equivalently, about 5 to about 8 cm, of skin contact), such that one or more antennas within the head 122 can send radio frequency (RF) signals to, and receive radio frequency (RF) signals from, an antenna (not shown) disposed within the hermetic enclosure of the implanted device 110 or disposed within a connector block 111 of the device 110, in accordance with common practice in the art.

Figure 2:
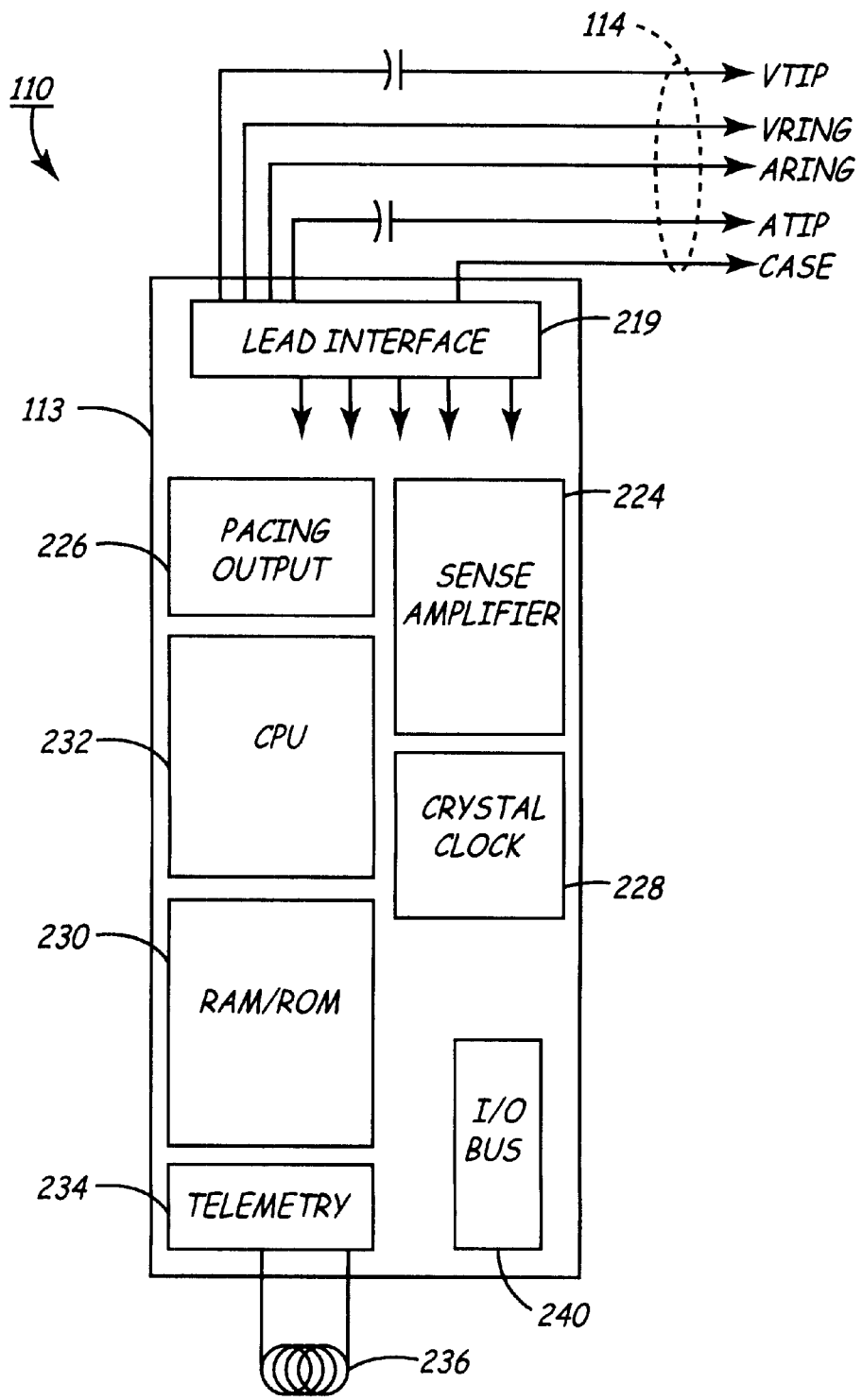

FIG. 2 provides a general block diagram of electronic circuitry that makes up the pacemaker 110. The pacemaker 110 is a device capable of performing a variety of functions, such as delivering electrical stimulation therapy to the patient 112 in accordance with the presently disclosed embodiment of the invention. FIG. 2 shows that pacemaker 110 comprises circuitry for controlling the device's pacing and sensing functions. Aspects of the pacemaker circuitry may be of conventional design, in accordance; for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random-access memory and read-only memory (RAM/ROM) unit 230, and a pacing timing and control circuit in the form of a programmed central processing unit (CPU) 232, all of which are well-known in the art.

The pacemaker 110 also includes an internal telemetry communications circuit 234 coupled to an antenna 236 so that it is capable of communicating with the external programmer/control unit 120. Various telemetry systems for providing the uplink and downlink communication channels between the external programming unit 120 and the implanted pacemaker 110 have been shown in the art and may be employed herein without departing from the spirit and scope of the instant invention. Exemplary communication telemetry systems that may be utilized herein are disclosed, for example, in the following U.S. Patents: U.S. Pat. No. 4,539,992 to Calfee et al. entitled "Method and Apparatus for Communicating With Implanted Body Function Stimulator," U.S. Pat. No. 4,550,732 to Batty Jr. et al. entitled "System and Process for Enabling a Predefined Function Within An Implanted Device," U.S. Pat. No. 4,751,589 to Slocum et al. entitled "Biomedical Implant With High Speed, Low Power Two-Way Telemetry," U.S. Pat. No. 4,676,248 to Berntson entitled "Circuit for Controlling a Receiver in an Implanted Device," U.S. Pat. No. 5,127,404 to Wyborny et al. entitled "Telemetry Format for Implanted Medical Device," U.S. Pat. No. 4,211, 235 to Keller, Jr. et al. entitled "Programmer for Implanted Device," U.S. Pat. No. 4,374,382 to Markowitz and U.S. Pat. No. 4,556,063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, the connections between the leads 114 and the various internal components of the pacemaker 110 are facilitated by a conventional connector block assembly 111, shown in FIG. 1 but not shown in FIG. 2. Electrically, the coupling of the leads 114 and the internal electrical components of the pacemaker 110 may be facilitated by a lead interface circuit 219, which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuitry 226, in accordance with common practice, such that cardiac electrical signals may be conveyed to the sense amplifier circuitry 224, and such that stimulating pulses may be delivered to cardiac tissue, via the leads 114.

It will be appreciated that the signals received over the leads 114 by the sense amplifier circuitry 224 may be collected and stored in the RAM/ROM unit 230 by the CPU 232 acting under control of software also stored in the RAM/ROM unit 230. Additional data, such as the timing of signals delivered by the stimulating pulse output circuitry 226 may also be stored in the RAM/ROM unit 230. This stored data may be later retrieved and delivered to the programming unit 120 via the telemetry communications circuit 234.

As previously noted, the circuitry of the pacemaker 110 includes the central processing unit (CPU) 232 which may be an off-the-shelf programmable microprocessor or microcontroller, but in the presently illustrated embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of a program of instructions stored in the RAM/ROM unit 230. The crystal clock 228 in the presently illustrated embodiment is a crystal controlled oscillator that provides a main timing clock signal. Again, the lines over which such clock signals are provided to the various components of the pacemaker 110 (e.g., the CPU 232) are omitted from FIG. 2 for the sake of clarity. It is believed that those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

Stimulating pulse output circuitry 226, which functions to generate cardiac stimuli under control of signals issued by the CPU 232, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 224, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pacemaker 110 in accordance with common practice in the art. In addition, these event-indicating signals, as discussed above, may be communicated, via the uplink communication channel, to the external programming unit 120 for storage and visual display to a physician or clinician.

Those of ordinary skill in the art will appreciate that the pacemaker 110 may include numerous other components and subsystems, for example, activity sensors and associated circuitry. The presence or absence of such additional components in the pacemaker 110, however, is not believed to be directly pertinent to the present invention, which relates generally to the firmware architecture of a portion of the RAM/ROM unit 230, permitting modular feature design for the pacemaker 110, and to the method of operation of this firmware architecture.

Figure 3:
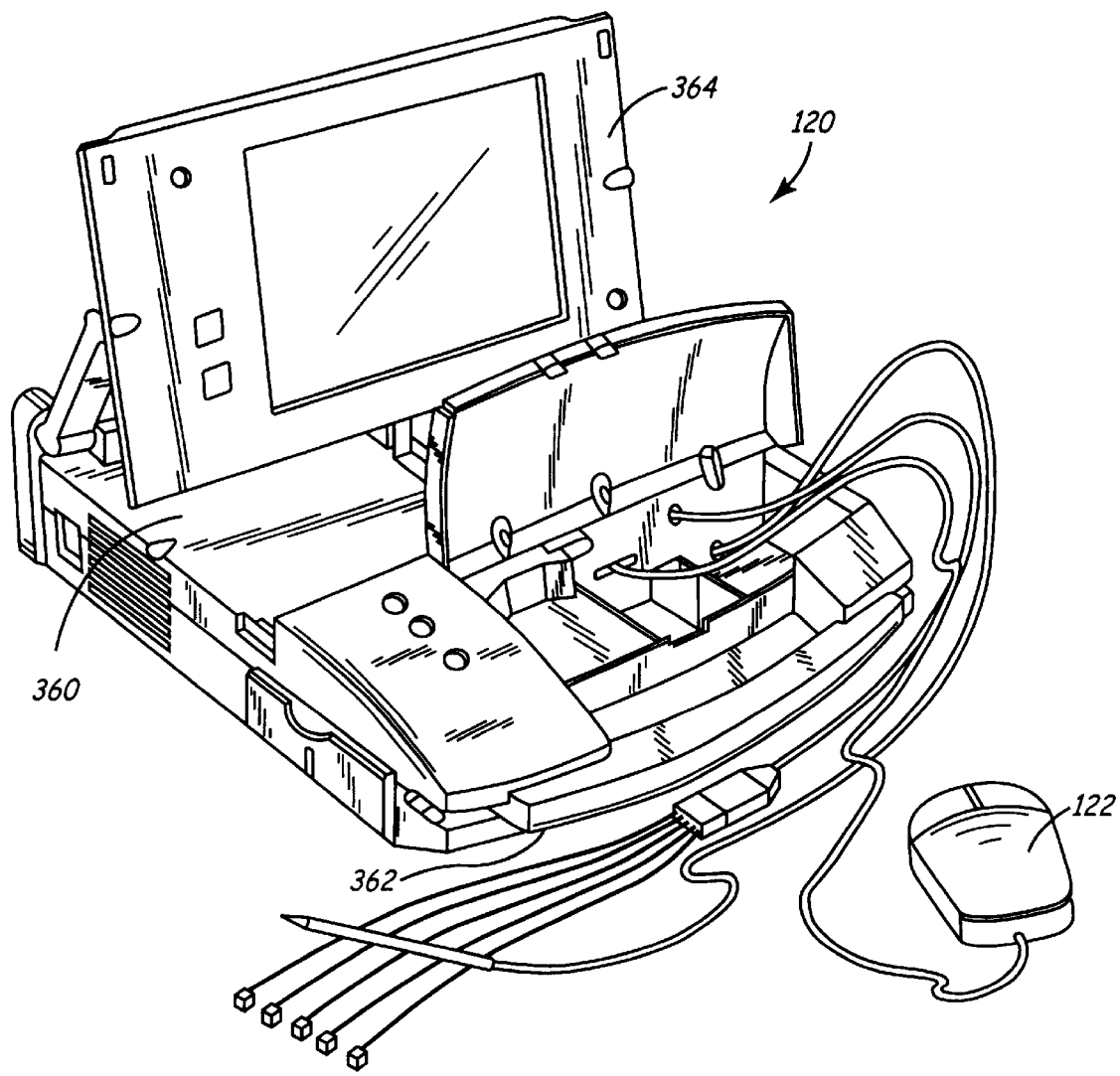

FIG. 3 shows a perspective view of one embodiment of the programming unit 120 in accordance with the presently disclosed embodiment of the invention. Internally, the programmer 120 includes a processing unit (not shown), which in accordance with the presently disclosed embodiment of the invention is a personal computer-type motherboard, for example, a computer motherboard including an Intel 80×86 microprocessor or the like and related circuitry such as digital memory.

Referring to FIG. 3, the programming unit 120 comprises an outer housing 360, which is preferably made of thermal plastic or another suitably rugged yet relatively lightweight material. A carrying handle, designated generally as 362 in FIG. 3, is integrally formed into the front of the housing 360. With the handle 362, the programming unit 120 can be carried like a briefcase.

An articulating display screen 364 is disposed on an upper surface of the housing 60. The display screen 364 folds down into a closed position (not shown) when the programming unit 120 is not in use, thereby reducing the size of the programming unit 120 and protecting the display surface of the display 364 during transportation and storage thereof.

A floppy disk drive is disposed within the housing 360 and is accessible via a disk insertion slot (not shown). A hard disk drive is also disposed within the housing 360, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 120 to adapt its mode of operation depending upon the type of implanted device to be programmed. Accordingly, it may be desirable to have an expansion cartridge containing EPROMS or the like for storing program information to control the programming unit 120 to operate in a particular manner corresponding to a given type of implantable device.

In accordance with the presently illustrated embodiment of the invention, the programming unit 120 is equipped with an internal printer (not shown) so that a hard copy of a patient's electrocardiogram (ECG) or of graphics displayed on the programmer's display screen 364 can be generated. Several types of printers, such as the AR-100 printer available from General Scanning Co., are known and commercially available.

In the perspective view of FIG. 3, the programming unit 120 is shown with the articulating display screen 364 having been lifted up into one of a plurality of possible open positions such that the display area thereof is visible to a user situated in front of the programming unit 120. The articulating display screen 364 is preferably of the LCD or electro-luminescent type, characterized by being relatively thin as compared, for example, a cathode ray tube (CRT) or the like.

The display screen 364 is operatively coupled to computer circuitry disposed within the housing 360, and is adapted to provide a visual display of graphics and/or data under control of the internal computer.

One embodiment of the programming unit 120 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
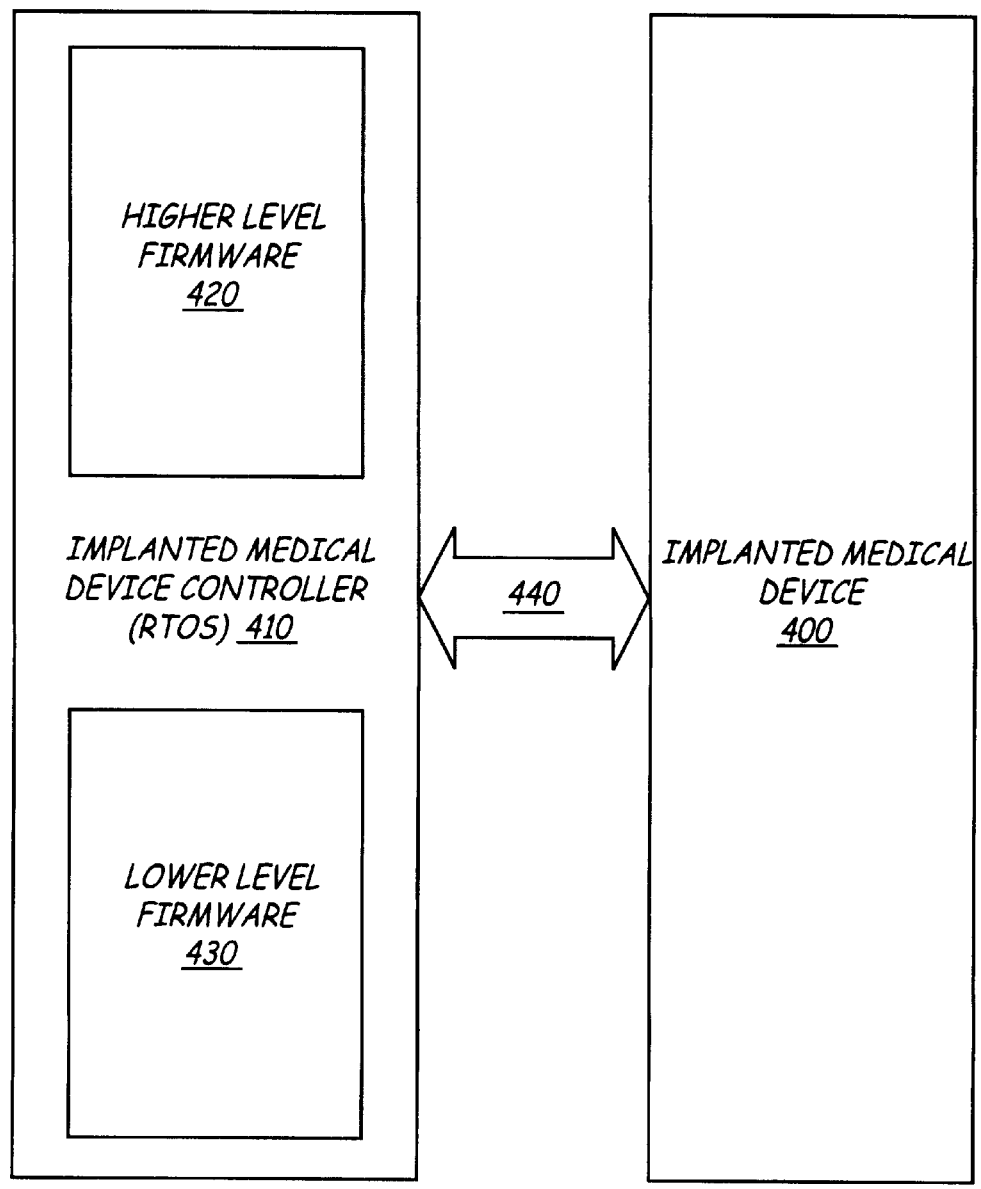

Turning to FIG. 4, a general block diagram of various illustrative embodiments of a device according the present invention is shown, comprising an implantable medical device (MD) 400 and an implantable medical device (IMD) controller 410 controlling the implantable medical device 400. The implantable medical device (IMD) 400 may comprise an implantable pulse generator (IPG) for an implantable pacemaker, such as an implantable anti-brady pacemaker and/or an implantable anti-tachy pacemaker. The implantable medical device (IMD) controller 410 may have higher level firmware 420 and lower level firmware 430. The implantable medical device (IMD) 400 and the implantable medical device (IMD) controller 410 may communicate via coupler 440. The implantable medical device (IMD) controller 410 uses a pre-emptive real-time operating system (RTOS). The implantable medical device (IEMD) controller 410 has a firmware architecture allowing at least one of modular feature design, modular feature implementation, extensible feature design and extensible feature implementation.

Figure 5:
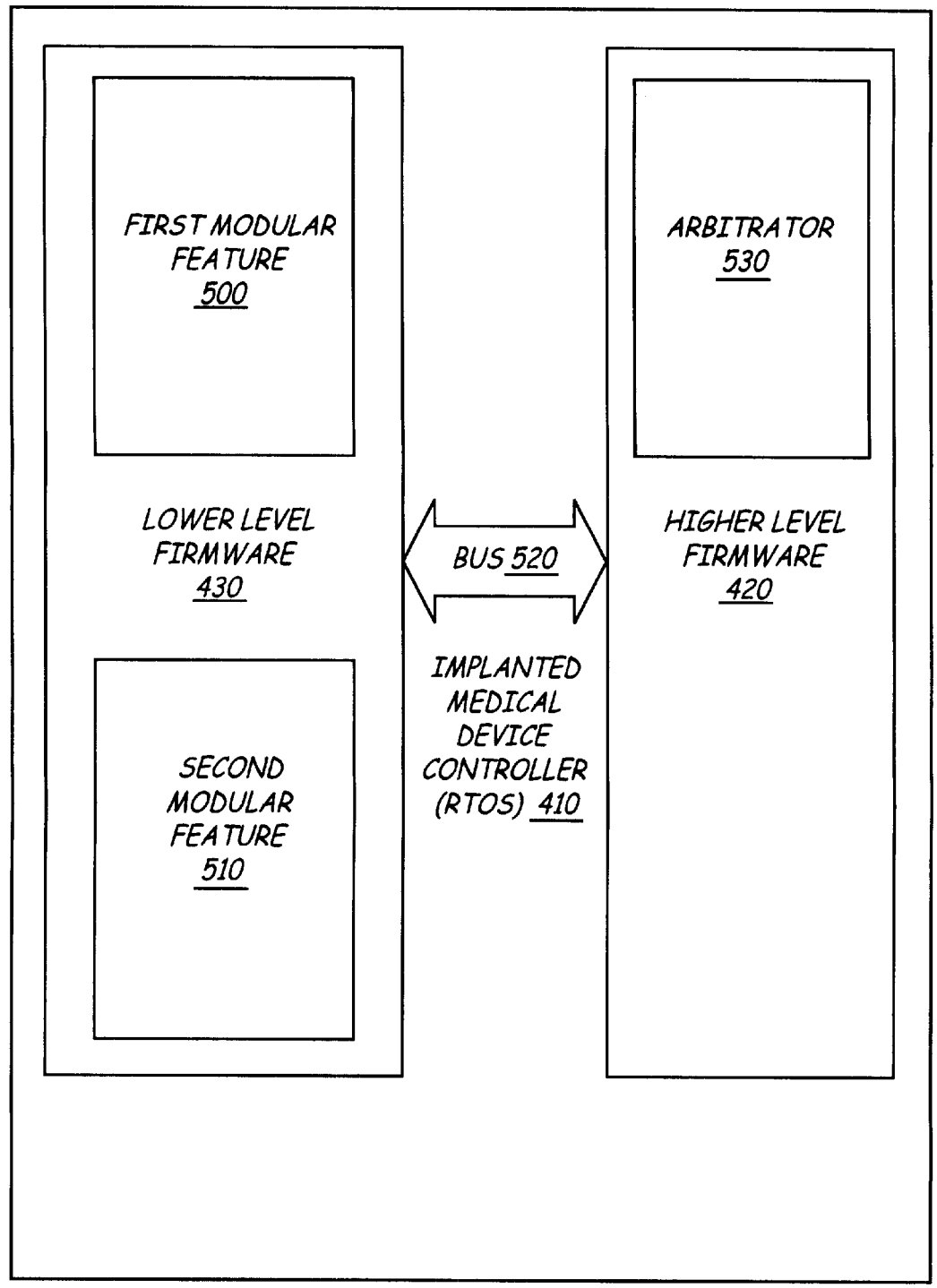

As shown in FIG. 5, the implantable medical device (IMD) controller 410 with the pre-emptive real-time operating system (RTOS) may have a plurality of modular features, such as first modular feature 500 and second modular feature 510. The firmware architecture of the implantable medical device (IMD) controller 410 may coordinate between and among the plurality of modular features, such as the first modular feature 500 and the second modular feature 510, to reduce feature-to-feature interactions.

The implantable medical device (IMD) controller 410 may also have a converter (not shown) enabling efficient conversion between at least one identifiable first modular feature, for example, the first modular feature 500, working in a rate domain (beats per minute or BPM), and at least one identifiable second modular feature, for example, the second modular feature 510, working in an interval domain (usually in milliseconds or msec). The converter may be included in the higher level firmware 420 and/or the lower level firmware 430. Alternatively, and/or additionally, the converter may be included elsewhere in the implantable medical device (IMD) controller 410. Some modular features output a desired pacing rate, and a higher level firmware "arbitrator" (such as firmware arbitrator 530 disposed in the higher level firmware 420, as shown in FIG. 5) may decide to use the desired pacing rate output by the modular feature or use another value from a different modular feature.

Figure 6:
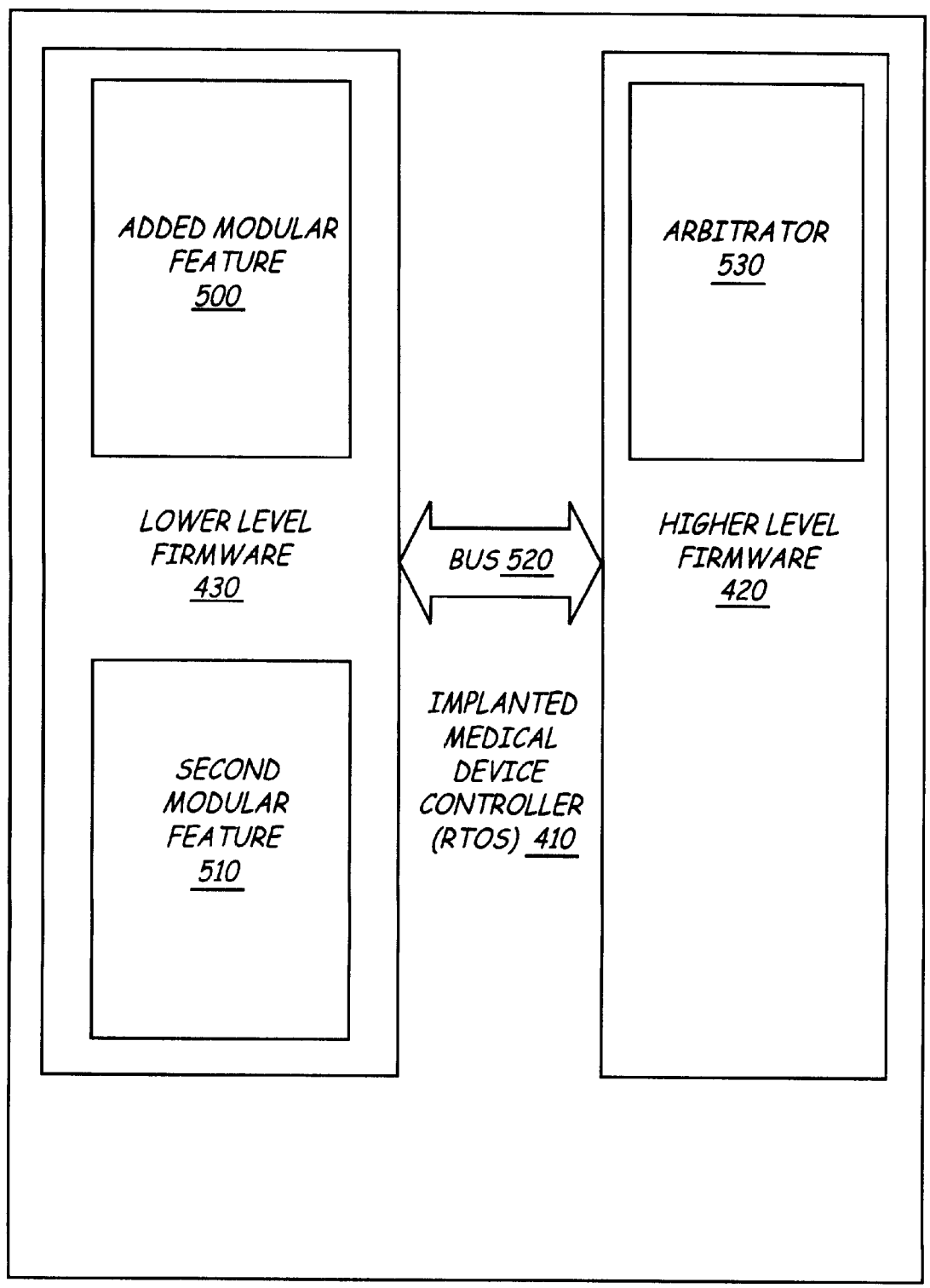
Figure 7:
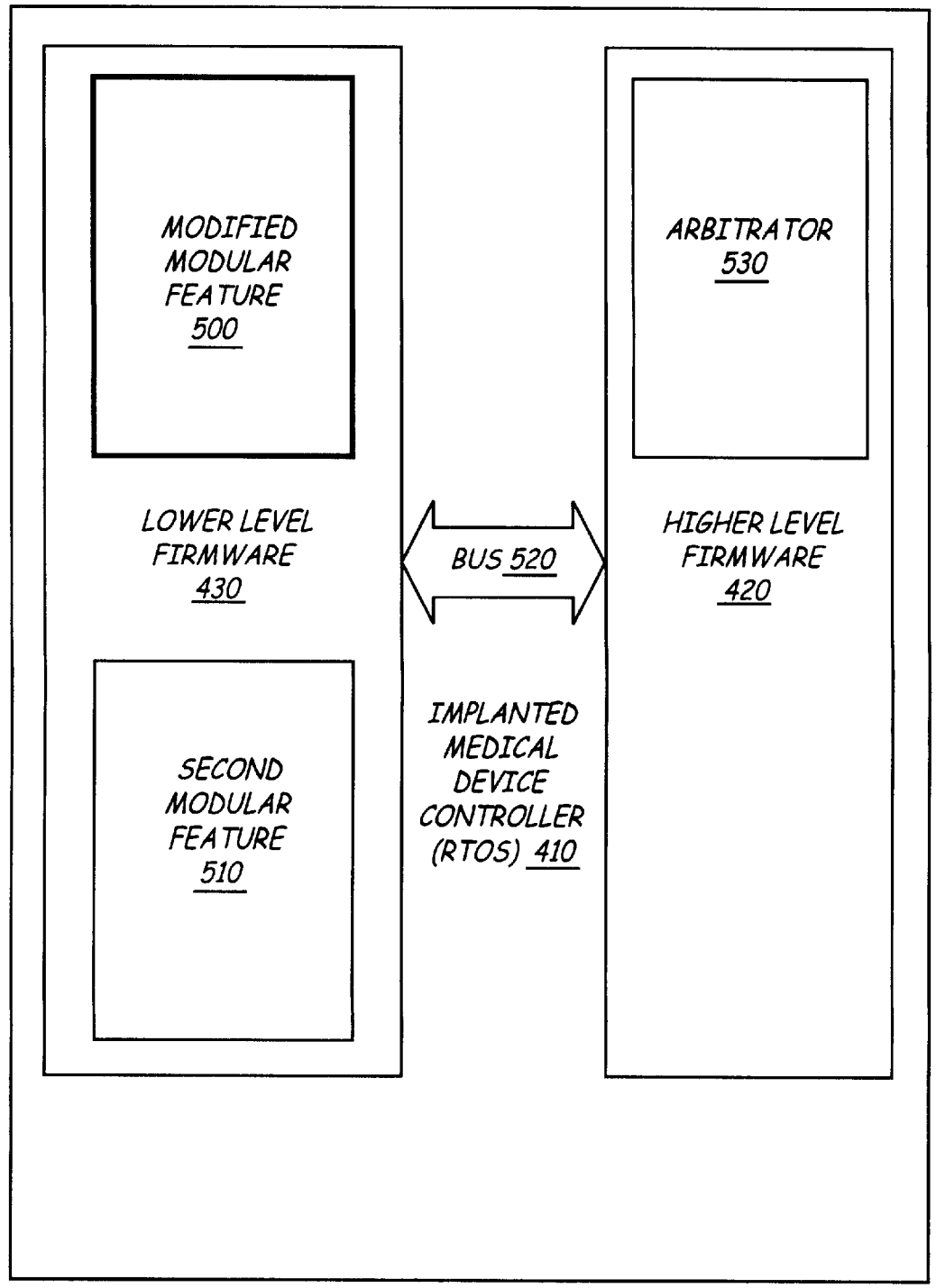
Figure 8:
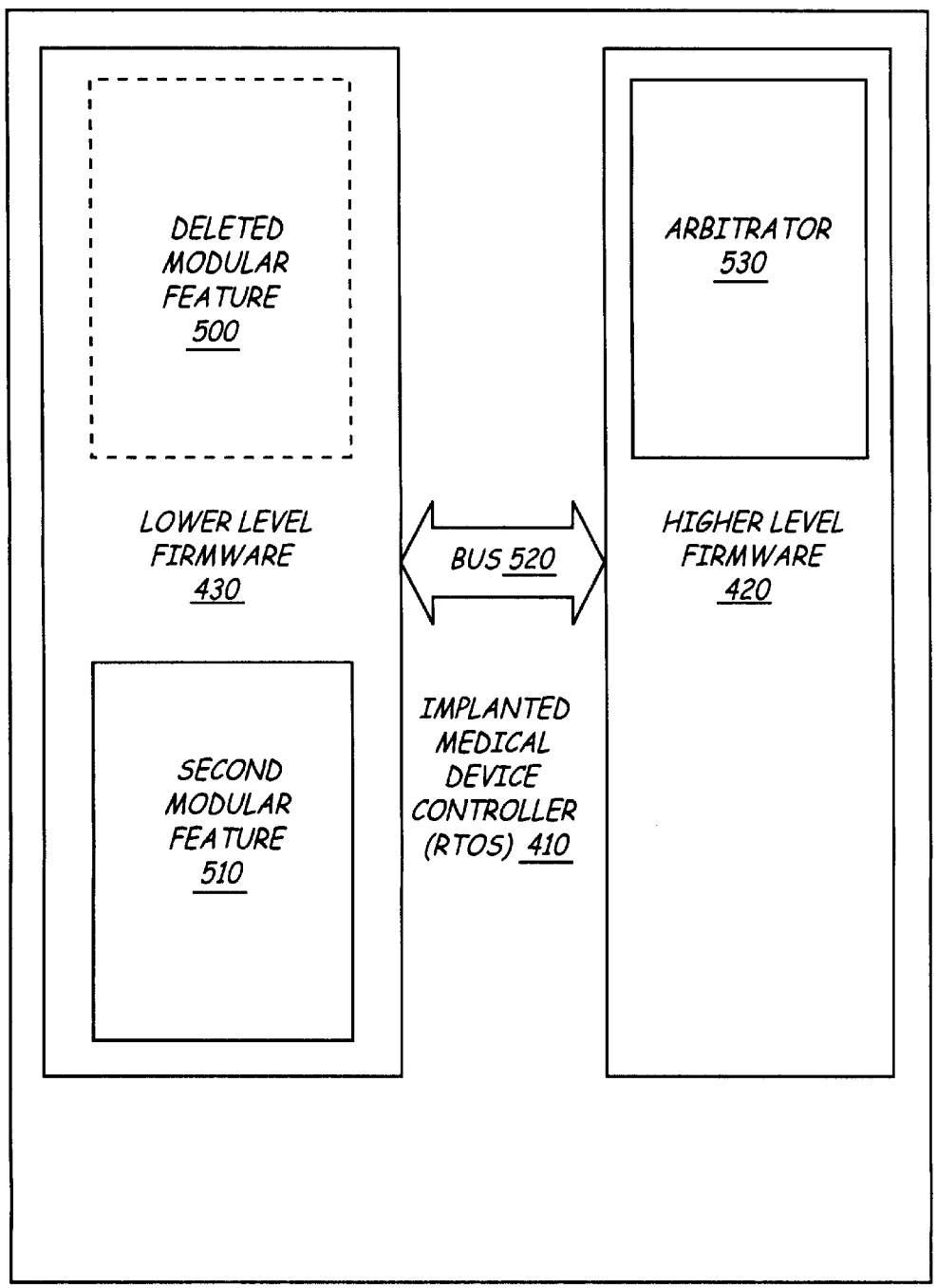

As shown in FIGS. 6–8, controlling the implantable medical device (IMD) 400 using the implantable medical device (IMD) controller 410 with the pre-emptive real-time operating system (RTOS) may comprise at least one of adding a modular feature to the firmware, modifying a modular feature of the firmware and deleting a modular feature from the firmware. As shown in FIG. 6, for example, controlling the implantable medical device (IMD) 400 using the implantable medical device (IMD) controller 410 may comprise adding a modular feature, such as added modular feature 600, to the lower level firmware 430. As shown in FIG. 7, for example, controlling the implantable medical device (IMD) 400 using the implantable medical device (IMD) controller 410 may comprise modifying a modular feature, such as modified modular feature 700, in the lower level firmware 430. As shown in FIG. 8, for example, controlling the implantable medical device (IMD) 400 using the implantable medical device (IMD) controller 410 may comprise deleting a modular feature, such as deleted modular feature 800 (shown in phantom), from the lower level firmware 430.

The implantable medical device (IMD) controller 410 firmware architecture, described in more detail below, allows at least one of modular feature design, modular feature implementation, extensible feature design and extensible feature implementation. In various illustrative embodiments, the firmware architecture itself, with the higher level firmware 420 communicating with and/or directing the lower level firmware 430 via bus 520, coordinates between and among the plurality of modular features, such as the first modular feature 500 and the second modular feature 510, to reduce feature-to-feature interactions.

Figure 9:
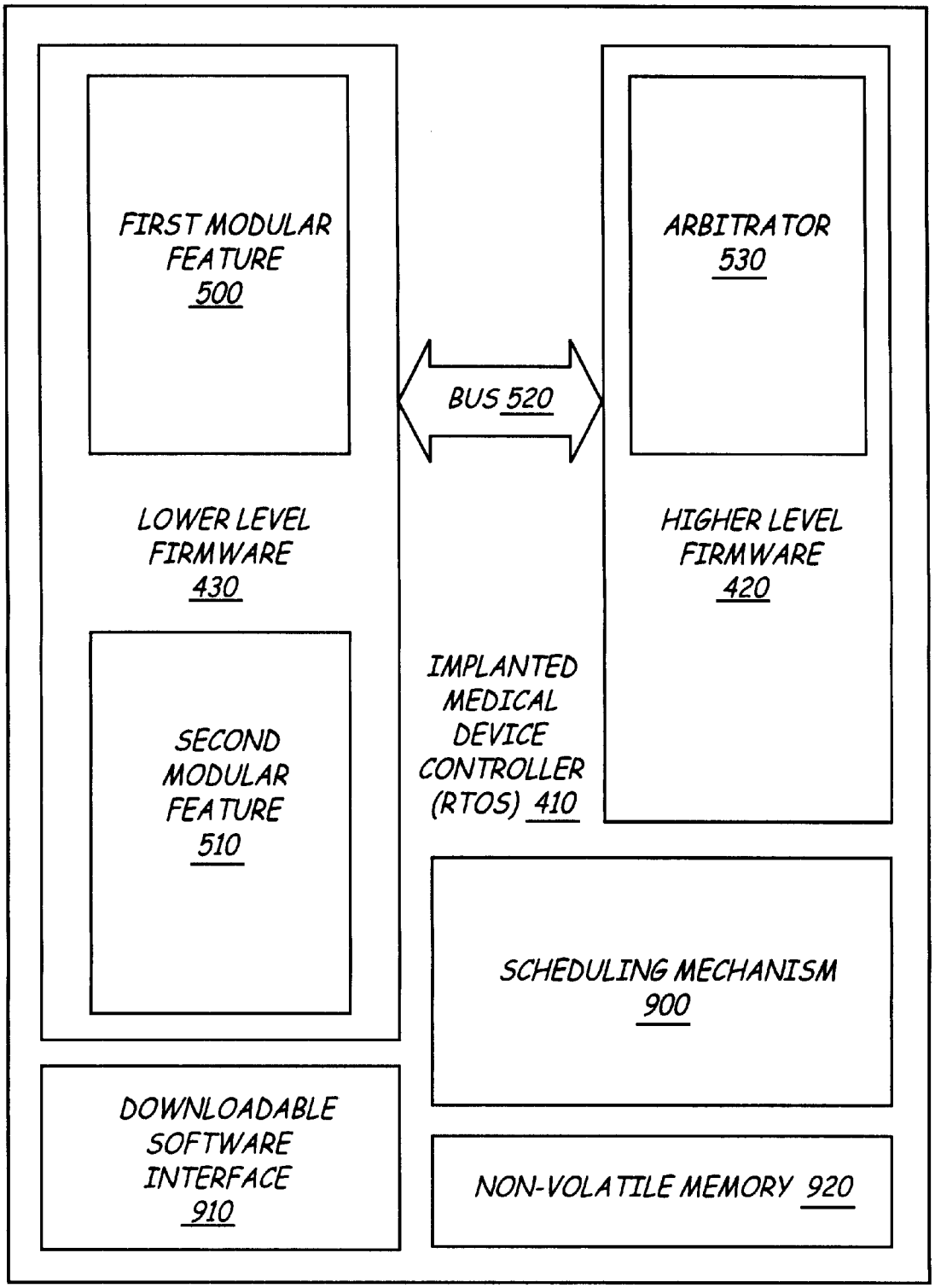

As shown in FIG. 9, the implantable medical device (IMD) controller 410 with the pre-emptive real-time operating system (RTOS) may have a scheduling mechanism 900. The implantable medical device (IMD) controller 410 may also have a downloadable software interface 910 and/or a non-volatile memory 920.

Figure 10:
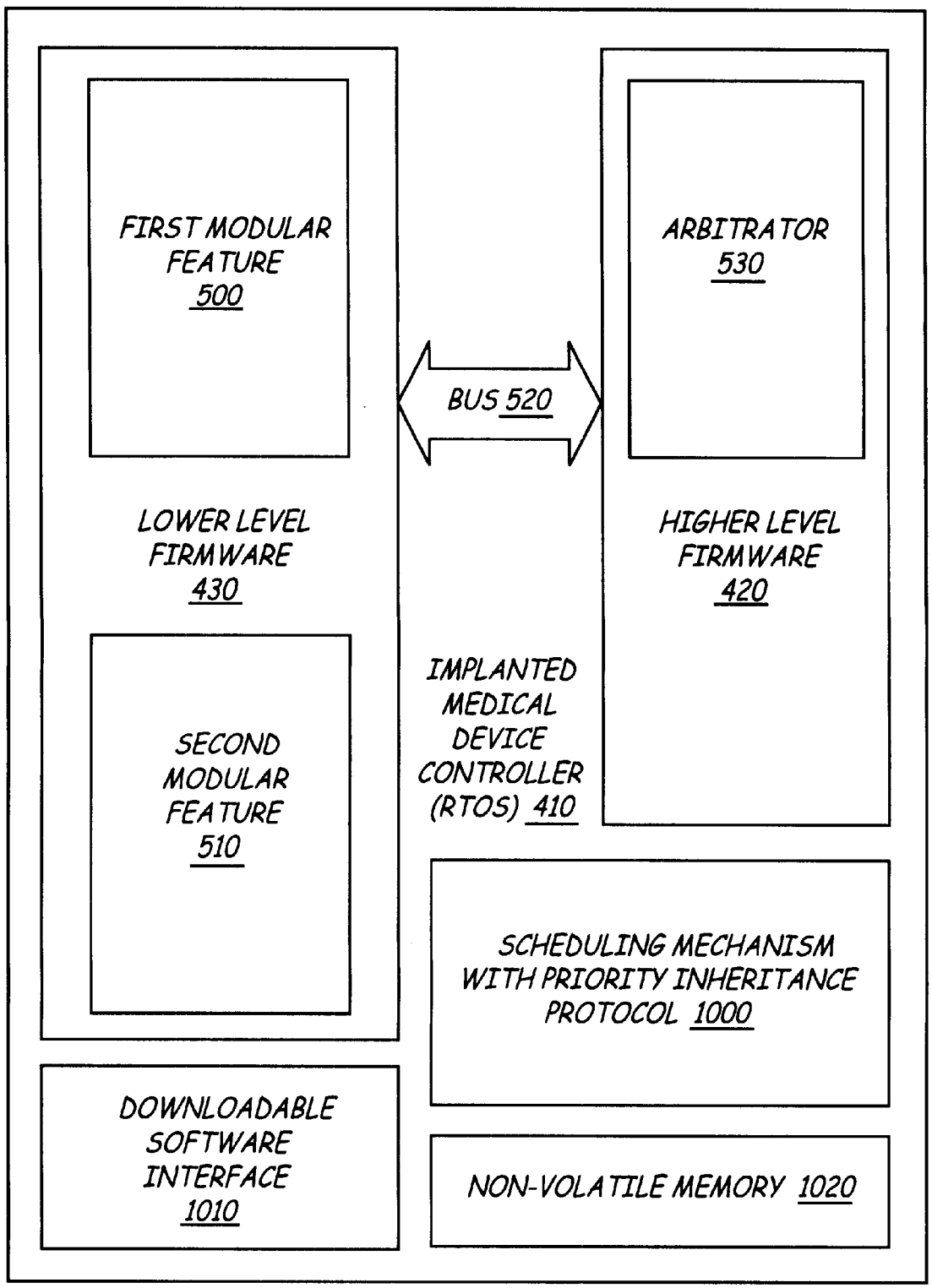

As shown in FIG. 10, the implantable medical device (IMD) controller 410 with the pre-emptive real-time operating system (RTOS) may have a scheduling mechanism 1000 with a priority inheritance protocol. The implantable medical device (IMD) controller 410 with the pre-emptive real-time operating system (RTOS) having the scheduling mechanism 1000 with the priority inheritance protocol may be capable of being analyzed using rate monotonic analysis. The implantable medical device (IMD) controller 410 with the pre-emptive real-time operating system (RTOS) having the scheduling mechanism 1000 with the priority inheritance protocol may be used in devices and/or systems that are resource-constrained, in terms of read-only memory (ROM), random access memory (RAM), power consumption, central processing unit (CPU) bandwidth, and the like. The implantable medical device (IMD) controller 410 with the pre-emptive real-time operating system (RTOS) having the scheduling mechanism 1000 with the priority inheritance protocol may also have a downloadable software interface 1010 and/or a non-volatile memory 1020.

Figure 11:
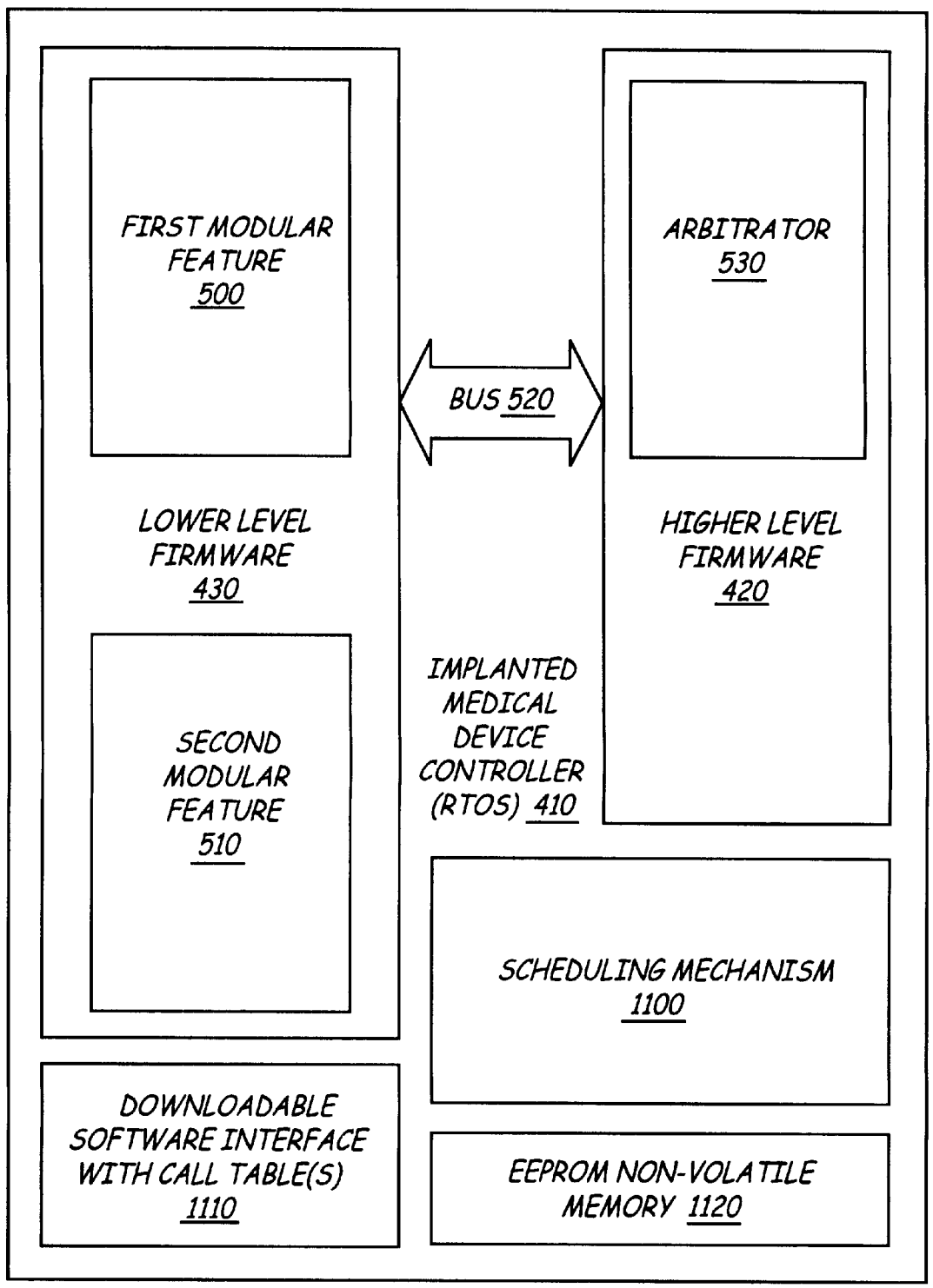

As shown in FIG. 11, the implantable medical device (IMD) controller 410 with the pre-emptive real-time operating system (RTOS) may have a scheduling mechanism 1100. The implantable medical device (IMD) controller 410 may also have a downloadable software interface 1110 with one or more call tables and/or an electrically erasable programmable read-only memory (EEPROM) non-volatile memory 1120.

Figure 12:
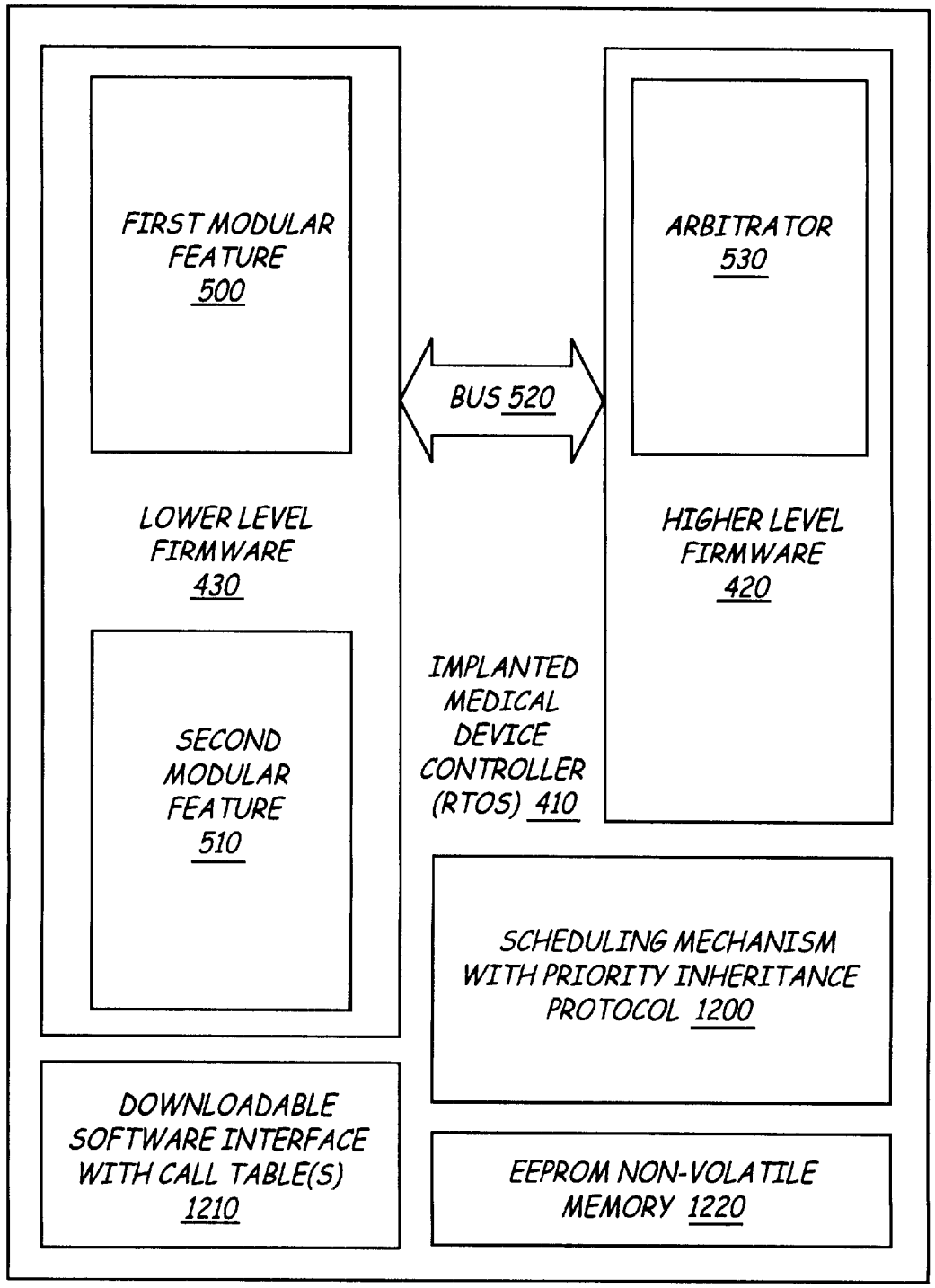

As shown in FIG. 12, the implantable medical device (IMD) controller 410 with the pre-emptive real-time operating system (RTOS) may have a scheduling mechanism 1200 with a priority inheritance protocol. The implantable medical device (IMD) controller 410 with the pre-emptive real-time operating system (RTOS) having the scheduling mechanism 1200 with the priority inheritance protocol may be capable of being analyzed using rate monotonic analysis. The implantable medical device (IMD) controller 410 with the pre-emptive real-time operating system (RTOS) having the scheduling mechanism 1200 with the priority inheritance protocol may be used in devices and/or systems that are resource-constrained, in terms of read-only memory (ROM), random access memory (RAM), power consumption, central processing unit (CPU) bandwidth, and the like. The implantable medical device (IMD) controller 410 with the pre-emptive real-time operating system (RTOS) having the scheduling mechanism 1200 with the priority inheritance protocol may also have a downloadable software interface 1210 with one or more call tables and/or an electrically erasable programmable read-only memory (EEPROM) non-volatile memory 1220.

The firmware architecture of the implantable medical device (IMD) controller 410 is designed to be modular and/or extensible and provides improved support for downloadable software, also known a RAMware. In various illustrative embodiments, the firmware architectural improvements include the use of a real-time operating system (RTOS) that provides pre-emptive scheduling and has facilities to prevent deadlock and unbounded priority inversion as well as support for rigorous timing analysis.

Downloadable software (RAMware) is the ability to load new software (executable code and not merely parameter values) into the implantable medical device (IMD) controller 410 via telemetry, for example, through a downloadable software interface 1210 with one or more call tables, as described above. This downloadable code (RAMware) may be backed up in an electrically erasable programmable read-only memory (EEPROM) non-volatile memory 1220, for example, so that the downloadable code (RAMware) could provide a permanent change to the therapy program for the implantable medical device (IMD) 400 that is capable of surviving a device reset.

The firmware architecture of the implantable medical device (IMD) controller 410, in various illustrative embodiments, uses pre-emption and allows downloadable software (RAMware) applications to create their own independent tasks. This is unlike conventional devices, as described above, in which the RAMware applications have to reside among the existing "tasks" in the embedded firmware, where the RAMware applications could create timing problems, making it difficult for the firmware to achieve all of the firmware deadlines.

The firmware architecture of the implantable medical device (IMD) controller 410, in various illustrative embodiments, makes use of event-driven intertask communication, call tables and a pre-emptive real-time operating system (RTOS). Consequently, the firmware architecture of the implantable medical device (IMD) controller 410, in these various illustrative embodiments, allows a downloadable software (RAMware) application to be designed in a similar manner to the design of a read-only memory (ROM)-resident application. The downloadable software (RAMware) applications in the implantable medical device (IMD) controller 410, in these various illustrative embodiments, have access to the full range of functionality provided in the embedded firmware, including all pre-emptive real-time operating system (RTOS) services. The downloadable software (RAMware) function calls may be inserted and/or appended to read-only memory (ROM)-resident function call tables. Alternatively, and/or additionally, the downloadable software (RAMware) function calls may replace read-only memory (ROM)-resident entities in the function call tables.

A downloadable software (RAMware) application in the implantable medical device (IMD) controller 410, in these various illustrative embodiments, may be created as a new foreground task. Similarly, since the downloadable software (RAMware) application in the implantable medical device (IMD) controller 410, in these various illustrative embodiments, may be backed up in an electrically erasable programmable read-only memory (EEPROM) non-volatile memory, the downloadable software (RAMware) application may be offered as a permanent, life-critical therapy without concern about being lost due to a device reset. Furthermore, a temporary downloadable software (RAMware) application, for research-oriented purposes, for example, may be downloaded "on top of" a permanent downloadable software (RAMware) application, allowing devices with permanent downloadable software (RAMware) applications to be included in research studies.

The downloadable software (RAMware) applications in the implantable medical device (IMD) controller 410, in various illustrative embodiments, may be thoroughly analyzed to allay concern for possible disruption of the proper functioning of read-only memory (ROM)-resident features, since the architecture may be subjected to rigorous timing analysis, due to inclusion of a priority inheritance protocol in the pre-emptive real-time operating system (RTOS).

The modular features may operate in the "rate domain," where calculations are performed in units of beats per minute (bpm). Using 8-bit values for these calculations can provide a resolution of 1 beat per minute (1 bpm) steps over a range from 0 bpm to 255 bpm ($2^8=256$), which is acceptable for brady and tachy therapy applications. In alternative illustrative embodiments, 16-bit values for calculations may be used that can provide a resolution of 1 operation per minute (1 oppm) steps over a range from 0 oppm to 65535 oppm ($2^{16}=65536$), which is acceptable for certain types of neurological therapy applications.

As described above, some modular features output a desired pacing rate, and a higher level firmware "arbitrator" (such as firmware arbitrator 530 disposed in the higher level firmware 420, as shown in FIG. 5) may decide to use the desired pacing rate output by the modular feature or use another value from a different modular feature. In the simplest form, the highest pacing rate is chosen by the higher level firmware arbitrator. In a more complex form, a higher pacing rate may lose priority to some modular feature that has a lower pacing rate. Some modular features output an offset value, and a higher level firmware operation may combine some or all of the offset values, for example, as in Atrial Ventricular (AV) adaptation. Some modular features may pass through one or more parameter values, either unmodified or modified, for example, as in a Sensing Atrial Ventricular (SAV) parameter value passing through an Auto Post-Ventricular Atrial Refractory algorithm.

During temporary operation, key pacing therapy parameters, such as Mode, Escape Interval, Pacing Atrial Ventricular (PAV) interval, Sensing Atrial Ventricular (SAV) interval, Post-Ventricular Atrial Refractory Period (PVARP), and the like, are held at static values and are not modified by modular features in the therapy flow. Consequently, modular features do not have to be disabled during temporary operations.

Each modular feature, such as the first modular feature 500 and the second modular feature 510, may be a firmware subroutine, for example, in the lower level firmware 430. Each modular feature firmware subroutine may be called by the higher level firmware 420. When each modular feature is called by the higher level firmware 420, the modular feature first checks to see if that particular modular feature is programmed to be "on," and then checks for mode pertinency. That particular modular feature algorithm continues to run if, and only if, all the checks pass (that particular modular feature is programmed to be "on" and is pertinent). Otherwise, that particular modular feature outputs a characteristic default value, such as the relevant rate or offset value, and/or an unmodified value, and ends.

Any of the above-disclosed embodiments of a method and a device according to the present invention enables therapy features to be modular and/or extensible and resolves many feature-to-feature interactions in implantable medical devices. Additionally, any of the above-disclosed embodiments of a method and a device according to the present invention enables features to be easily and quickly added and/or modified and/or deleted in a given design and may create interim values for therapy features, simplifying the development and/or testing of those features. Furthermore, any of the above-disclosed embodiments of a method and a device according to the present invention enables features to operate in the "rate domain" in beats per minute (bpm), may make strategic conversions into the "interval domain" for parameter values that are loaded into hardware timing circuitry, may clearly identify where modular feature algorithms are working in the rate domain and/or in the interval domain and enables efficient use of conversion between the rate domain and the interval domain.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values, in the sense of Georg Cantor. Accordingly, the protection sought herein is as set forth in the claims below.

What is claimed:

1. A method comprising:
   controlling an implantable medical device using a controller implementing a pre-emptive real-time operating system (RTOS) having a scheduling mechanism, the controller having a firmware architecture allowing at least one of modular feature design, modular feature implementation, extensible feature design and extensible feature implementation;

analyzing the pre-emptive real-time operating system (RTOS) using rate monotonic analysis;

providing an interface with downloadable software for the implantable medical device; and backing up at least some of the downloadable software using a non-volatile memory device, protecting the at least some of the downloadable software from a reset of the implantable medical device.

2. A method comprising:

controlling an implantable medical device using a controller implementing a pre-emptive real-time operating system (RTOS) having a scheduling mechanism, the controller having a firmware architecture allowing at least one of modular feature design, modular feature implementation, extensible feature design and extensible feature implementation;

analyzing the pre-emptive real-time operating system (RTOS) using rate monotonic analysis comprising using a priority inheritance protocol in the scheduling mechanism of the pre-emptive real-time operating system (RTOS);

providing an interface with downloadable software for the implantable medical device; and backing up at least some of the downloadable software using a non-volatile memory device, protecting the at least some of the downloadable software from a reset of the implantable medical device.

3. The method of claim 2, wherein controlling the implantable medical device using the controller comprises controlling a pulse generator for an implantable pacemaker.

4. The method of claim 3, wherein controlling the pulse generator for the implantable pacemaker comprises controlling the pulse generator for at least one of an implantable anti-brady pacemaker and an implantable anti-tachy pacemaker.

5. The method of claim 4, wherein providing the interface with downloadable software for the implantable medical device comprises using call tables and backing up the at least some of the downloadable software using the non-volatile memory device comprises using an electrical erasable programmable read-only memory (EEPROM) device.

6. The method of claim 3, wherein providing the interface with downloadable software for the implantable medical device comprises using call tables and backing up the at least some of the downloadable software using the non-volatile memory device comprises using an electrical erasable programmable read-only memory (EEPROM) device.

7. The method of claim 2, wherein providing the interface with downloadable software for the implantable medical device comprises using call tables, and backing up the at least some of the downloadable software using the non-volatile memory device comprises using an electrical erasable programmable read-only memory (EEPROM) device.

8. The method of claim 2, wherein providing the interface with downloadable software for the implantable medical device comprises using call tables and backing up the at least some of the downloadable software using the non-volatile memory device comprises using an electrical erasable programmable read-only memory (EEPROM) device.

9. A device comprising:

an implantable medical device;

a controller controlling the implantable medical device, the controller using a pre-emptive real-time operating system (RTOS) having a scheduling mechanism, the controller having a firmware architecture allowing at least one of modular feature design, modular feature implementation, extensible feature design and extensible feature implementation, the pre-emptive real-time operating system (RTOS) capable of being analyzed using rate monotonic analysis;

an interface interfacing with downloadable software for the implantable medical device; and a non-volatile memory device backing up at least some of the downloadable software, non-volatile memory device capable of protecting the at least some of the downloadable software from a reset of the implantable medical device.

10. A system comprising:

an implantable medical device;

a controller controlling the implantable medical device the controller using a pre-emotive real-time operating system (RTOS) having a scheduling mechanism, the controller having a firmware architecture allowing at least one of modular feature design, modular feature implementation, extensible feature design and extensible feature implementation, the pre-emptive real-time operating system: (RTOS) capable of being analyzed using rate monotonic analysis comprising a priority inheritance protocol;

an interface interfacing with downloadable software for the implantable medical device; and a non-volatile memo device backing up at least some of the downloadable software, non-volatile memory device capable of protecting the at least some of the downloadable software from a reset of the implantable medical device.

11. The system of claim 10, wherein the controller controls a pulse generator for an implantable pacemaker.

12. The system of claim 11, wherein the controller controls the pulse generator for at least one of an implantable anti-brady pacemaker and an implantable anti-tachy pacemaker.

13. The system of claim 12, wherein the interface interfacing with downloadable software for the implantable medical device comprises call tables and the non-volatile memory device backing up the at least some of the downloadable software comprises an electrical erasable programmable read-only memory (EEPROM) device.

14. The system of claim 11, wherein the interface interfacing with downloadable software for the implantable medical device comprises call tables and the non-volatile memory device backing up the at least some of the downloadable.

15. The system of claim 10, wherein the interface interfacing with downloadable software for the implantable medical device comprises call tables and the non-volatile memory device backing up the at least some of the downloadable software comprises an electrical erasable programmable read-only memory (EEPROM) device.

16. A system comprising:

an implantable medical device;

a controller controlling the implantable medical device, the controller using a pre-emptive real-time operating system (RTOS) having a scheduling mechanism, the controller having a firmware architecture allowing at least one of modular feature design, modular feature implementation, extensible feature design and extensible feature implementation, the pre-emptive real-time operating system (RTOS) capable of being analyzed using rate monotonic analysis;

an interface accessing downloadable software for the implantable medical device comprising call tables; and a non-volatile memory device backing up at least some of the downloadable software, the non-volatile memory device being capable of protecting the downloadable software from a reset of the implantable medical device and comprising an electrical erasable programmable mad-only memory (EEPROM) device.

17. A device comprising:

means for controlling an implantable medical device using a controller using a pre-emptive real-time operating system (RTOS) having a scheduling mechanism, the controller having a firmware architecture allowing at least one of modular feature design, modular feature implementation, extensible feature design and extensible feature implementation;

means for analyzing the pre-emptive real-time operating system (RTOS) using rate monotonic analysis;

means for providing an interface with downloadable software for the implantable medical device; and means for backing up at least some of the downloadable software using a non-volatile memory device, protecting the at least some of the downloadable software from a reset of the implantable medical device.

18. A system comprising:

means for controlling an implantable medical device using a controller using a pre-emptive real-time operating system (RTOS) having a scheduling mechanism, the controller having a firmware architecture allowing at least one of modular feature design, modular feature implementation, extensible feature design and extensible feature implementation;

means for analyzing the pre-emptive real-time operating system (RTOS) using rate monotonic analysis using a priority inheritance protocol in the scheduling mechanism of the pre-emptive real-time operating system (RTOS);

means for providing an interface with downloadable software for the implantable medical device: and means for backing up at least some of the downloadable software using a non-volatile memory device, protecting the at least some of the downloadable software from a reset of the implantable medical device.

19. The system of claim 18, wherein the means for controlling the implantable medical device using the controller comprises controlling a pulse generator for an implantable pacemaker.

20. The system of claim 19, wherein the means for providing the interface with downloadable software for the implantable medical device comprises using call tables and the means for backing up the at least some of the downloadable software using the non-volatile memory device comprises using an electrical erasable programmable read-only memory (EEPROM) device.

21. The system of claim 13, wherein the means for controlling the pulse generator for the implantable pacemaker comprises controlling the pulse generator for at least one of an implantable anti-brady pacemaker and an implantable anti-tachy pacemaker.

22. The system of claim 21, wherein the means for providing the interface with downloadable software for the implantable medical device comprises using call tables and the means for backing up the at least some of the downloadable software using the non-volatile memory device comprises using an electrical erasable programmable read-only memory (EEPROM) device.

23. The system of claim 18, wherein the means for providing the interface with downloadable software for the implantable medical device comprises using call tables and the means for backing up the at least some of the downloadable software using the non-volatile memory device comprises using an electrical erasable programmable read-only memory (EEPROM) device.

24. A system comprising:

means for controlling an implantable medical device using a controller using a pre-emptive real-time operating system (RTOS) having a scheduling mechanism, the controller having a firmware architecture allowing at least one of the modular feature design, modular feature implementation, extensible feature design and extensible feature implementation;

means for analyzing the pre-emptive real-time operating system (RTOS) using rate monotonic analysis;

means for providing an interface with downloadable software for the implantable medical device comprising call tables; and means for backing up at least some of the downloadable software using an electrical erasable programmable read-only memory (EEPROM) device and for protecting the downloadable software from a reset of the implantable medical device.

\* \* \* \* \*

UNITED STATES PATENT AND TRADEMARK OFFICE
CERTIFICATE OF CORRECTION

PATENT NO. : 6,584,356 B2
DATED : June 24, 2003
INVENTOR(S) : Paul G. Wassmund et al.

It is certified that error appears in the above-identified patent and that said Letters Patent is hereby corrected as shown below:

Column 14,
Line 21, delete "pre-emotive", replace with -- pre-emptive --.

Column 16,
Line 10, delete "claim 13", replace with -- claim 19 --.

Signed and Sealed this

Eighteenth Day of January, 2005

JON W. DUDAS
*Director of the United States Patent and Trademark Office*